United States Patent
Hardigan

(10) Patent No.: US 8,521,490 B2
(45) Date of Patent: Aug. 27, 2013

(54) STATISTICAL MODEL FOR PREDICTING FALLING IN HUMANS

(75) Inventor: Patrick C. Hardigan, Fort Lauderdale, FL (US)

(73) Assignee: Nova Southeastern University, Fort Lauderdale, FL (US)

( * ) Notice: Subject to any disclaimer, the term of this patent is extended or adjusted under 35 U.S.C. 154(b) by 410 days.

(21) Appl. No.: 12/895,097

(22) Filed: Sep. 30, 2010

(65) Prior Publication Data

US 2011/0082672 A1    Apr. 7, 2011

Related U.S. Application Data

(60) Provisional application No. 61/248,193, filed on Oct. 2, 2009, provisional application No. 61/253,171, filed on Oct. 20, 2009.

(51) Int. Cl.
*G06F 9/455*    (2006.01)

(52) U.S. Cl.
USPC ................................................ 703/6; 600/595

(58) Field of Classification Search
USPC ................... 703/6, 11; 705/3; 600/301, 558, 600/595; 348/152; 382/104; 707/104.1
See application file for complete search history.

(56) References Cited

U.S. PATENT DOCUMENTS

| | | | |
|---|---|---|---|
| 2003/0228033 A1* | 12/2003 | Daniel et al. | 382/104 |
| 2008/0009686 A1* | 1/2008 | Hendrich | 600/301 |
| 2008/0281638 A1* | 11/2008 | Weatherly et al. | 705/3 |
| 2008/0287752 A1* | 11/2008 | Stroetz et al. | 600/301 |
| 2009/0030945 A1* | 1/2009 | Miller et al. | 707/104.1 |
| 2009/0278934 A1* | 11/2009 | Ecker et al. | 348/152 |
| 2010/0049095 A1* | 2/2010 | Bunn et al. | 600/595 |
| 2010/0228144 A1* | 9/2010 | Labat | 600/558 |

OTHER PUBLICATIONS

Spencer, B.D., "When do latent class models overstate accvuracy for binary classifiers: With Applications to Jury Accuracy, Survey Response Error", and Diagnostic Error, Northwestern University, Nov. 2008.*
Ubersex JS. LCA Frequently asked questions (FAQ). Mar. 4, 2008. Available at http://www.studygs.netlcitation/ama.htm. Accessed Dec. 1, 2008.
Falls Prevention Act of 2003. §S. 1217.
Weir E, Culmer L. Fall prevention in the elderly population. CMAJ 2004; 171: 724.

(Continued)

*Primary Examiner* — Kandasamy Thangavelu
(74) *Attorney, Agent, or Firm* — Fleit Gibbons Gutman Bongini & Bianco PL; Paul D. Bianco; Gary S. Winer

(57) ABSTRACT

Dependent variables believed to contribute to a likelihood of falling are analyzed using a latent class analysis. The dependent variables are biomedical factors, which may include, for example, arthritis, high blood pressure, diabetes, foot disorders, Parkinson's Disease, stroke, eye disorder, limb disorder, or proprioceptive disorder. Data pertaining to the biomedical factors is gathered from a population of individuals at risk of falling. Covariate data, including for example age and the number of prescriptions taken, is further analyzed against latent class data. For a particular group of at risk individuals, a set of five classes produced useful results broadly corresponding to groups representing individuals who have: good health; a range of diseases; Parkinson's Disease; arthritis; and high blood pressure. A probability of falling is determined, relative to the group of individuals with good health.

20 Claims, 3 Drawing Sheets

(56) References Cited

OTHER PUBLICATIONS

Tinetti ME. Preventing falls in elderly persons. N Engl J Med 2003; 348: 42-49.

Kannus P, Sievnen H, Palvanen M, et al. Prevention of falls and consequent injuries in elderly people. Lancet 2005; 366: 1885-1893.

Kannus P, Palvanen M, Niemi S. Time trends in severe head injuries among elderly Finns. JAMA 2001; 286: 673-674.

Croudace TJ, Jarvelin MR, Wadsworth ME, Jones PB. Developmental typology of trajectories to nighttime bladder control: Epidemiologic application of longitudinal latent class analysis. American Journal of Epidemiology, 2003;157: 834-842.

Ploubidis GB, Abbott RA, Huppert FA, Kuh O, Wadsworth EJ, Croudace TJ. Improvements in social functioning reported by a birth cohort in mid-adult life: A person-centred analysis of GHQ-28 social dysfunction items using latent class analysis. Personality and Individual Differences. 2007;42:305-316.

Langeheine R, Pannekoek J, van de Pol F. Bootstrapping goodness-of-fit measures in categorical data analysis, Sociological Methods and Research. 1996;24:492-516.

Cathal Breathnach, Latent Class Analysis Identification of Syndromes in Alzheimer's Disease: A Bayesian Approach, Available at http://www.tcd.is/Statistics/postgraduate/0601.pdf., retrieved Dec. 1, 2008, pp. 1-19.

Patrick C. Hardigan, An Application of Latent Class Analysis in the Measurement of Falling Among a Community Elderly Population, The Open Medicine Journal, dated Feb. 24, 2009, vol. 2, pp. 12-17.

Hagenaars JA, McCutcheon AL, eds. Applied Latent Class Analysis. New York, NY: Cambridge University Press; 2002.

Lazarsfeld PF, Henry NW. Latent structure analysis. Boston: Houghton;1968.

McCutcheon AC. Latent class analysis. Beverly Hills: Sage;1987.

Kannus Lord SR, Sherrington C, Menz H. Falls in older people: risk factors and strategies for prevention. Cambridge: Cambridge University Press, 2001.

Everitt BS. The analysis of contingency tables. London: Chapman & Hall; 1992.

Everitt BS, Hand OJ. Finite mixture distributions. London: Chapman & Hall;1991.

Magidson J, Vermunt JK. Latent class models for clustering: A comparison with K-means, Canadian Journal of Marketing Research. 2002;20:37-44.

Clogg CC., Latent class models. In: G. Arminger, C.C. Clogg and M.E. Sobel, Editors, Handbook of statistical modelling for the social and behavioral sciences. New York: Plenum;1995.

Read TR, Cressie N. Goodness-of-fit statistics for discrete multivariate data. New York: Springer; 1988.

Lewis-Beck MS, Bryman A, Liao TF. eds. The Sage Encyclopedia of Social Science Research Methods. New York: Sage Publications Inc ;2004.

Cummings RG. Epidemiology of medication-related falls and fractures in the elderly. Drugs and Aging 1998; 12(1): 43-53.

* cited by examiner

1=Arthritis, 2=High Blood Pressure, 3=Diabetes, 4=Heart Disease, 5= Foot Disorders, 6=Parkinson's Disease, 7=Stroke Victim

STATISTICAL MODEL FOR PREDICTING FALLING IN HUMANS

CROSS REFERENCE TO RELATED APPLICATIONS

This invention claims the benefit of related U.S. Provisional Application Ser. Nos. 61/248,193, filed Oct. 2, 2009, and 61/253,171, filed Oct. 20, 2009, the contents of each of which are incorporated herein by reference.

FIELD OF THE INVENTION

The present invention relates to statistical measures for predicting sets of individuals at risk of falling and suffering harm.

BACKGROUND OF THE INVENTION

Herein, reference values in brackets ([ ]) refer to the references listed below, all of which are hereby incorporated by reference herein, in their entirety.

Falls among the elderly are a major public health concern. Research on falls and fall-related behavior among the elderly has found the following [5-11]:

1. Falls are the leading cause of injury deaths among individuals who are over 65 years of age.
2. By 2030, the population of individuals who are 65 years of age or older will double. By 2050, the population of individuals who are 85 years of age or older will quadruple.
3. In 2000, falls among elderly individuals accounted for 10,200 deaths and 1.6 million emergency department visits.
4. Sixty percent of fall-related deaths occur among individuals who are 75 years of age or older. Twenty-five percent of elderly persons who sustain a hip fracture die within one year.
5. Hospital admissions for hip fractures among the elderly have increased from 231,000 admissions in 1988 to 332,000 in 1999. The number of hip fractures is expected to exceed 500,000 by 2040.
6 Annually, more than 64,000 individuals who are over 65 years of age sustain a traumatic brain injury as a result of a fall.
7 Annually, 40,000 individuals who are over 65 years of age visit emergency departments with traumatic brain injuries suffered as a result of a fall, of which 16,000 of these individual are hospitalized and 4,000 of these individuals die.
8. The rate of fall-induced traumatic brain injuries for individuals who are 80 years of age or older increased by 60 percent from 1989 to 1998.
9. The estimated total cost for non-fatal traumatic brain injury-related hospitalizations for falls in individuals who are 65 years of age or older is more than $3.25 billion. Two-thirds of these costs occurred among individual who were 75 years of age or older.
10. The costs to the Medicare and Medicaid programs and society as a whole from falls by elderly persons continue to climb much faster than inflation and population growth. Direct costs alone will exceed $3.2 billion in 2020.

REFERENCES

1. Ubersex J S. LCA *Frequently asked questions* (FAQ). 4 Mar. 2008. Available at http://www.studygs.netlcitation/ama.htm. Accessed Dec. 1, 2008.
2. Hagenaars J A, McCutcheon A L, eds. *Applied Latent Class Analysis*. New York, N.Y.: Cambridge University Press; 2002.
3. Lazarsfeld P F, Henry N W. *Latent structure analysis*. Boston: Houghton; 1968.
4. McCutcheon A C. *Latent class analysis*. Beverly Hills: Sage; 1987.
5. Falls Prevention Act of 2003. §S. 1217.
6. Cummings R G. Epidemiology of medication-related falls and fractures in the elderly. *Drugs and Aging* 1998; 12(1): 43-53.
7. Kannus Lord S R, Sherrington C, Menz H. Falls in older people: risk factors and strategies for prevention. Cambridge: Cambridge University Press, 2001.
8. Weir E, Culmer L. Fall prevention in the elderly population. *CMAJ* 2004; 171: 724.
9. Tinetti M E. Preventing falls in elderly persons. *N Engl J Med* 2003; 348: 42-49.
10. Kannus P, Sievnen H, Palvanen M, et al. Prevention of falls and consequent injuries in elderly people. *Lancet* 2005; 366: 1885-1893.
11. Kannus P, Palvanen M, Niemi S. Time trends in severe head injuries among elderly Finns. *JAMA* 2001; 286: 673-674.
12. Croudace T J, Jarvelin M R, Wadsworth M E, Jones P B. Developmental typology of trajectories to nighttime bladder control: Epidemiologic application of longitudinal latent class analysis. *American Journal of Epidemiology*, 2003; 157: 834-842.
13. Everitt B S. *The analysis of contingency tables*. London: Chapman & Hall; 1992.
14. Everitt B S, Hand O J. *Finite mixture distributions*. London: Chapman & Hall; 1991.
15. Magidson J, Vermunt J K. Latent class models for clustering: A comparison with K-means, *Canadian Journal of Marketing Research*. 2002; 20:37-44.
16. Ploubidis G B, Abbott R A, Huppert F A, Kuh 0, Wadsworth E J, Croudace T J. Improvements in social functioning reported by a birth cohort in mid-adult life: A person-centred analysis of GHQ-28 social dysfunction items using latent class analysis. *Personality and Individual Differences*. 2007; 42:305-316.
17. Clogg C C., Latent class models. In: G. Arminger, C. C. Clogg and M. E. Sobel, Editors, *Handbook of statistical modelling for the social and behavioral sciences*. New York: Plenum; 1995.
18. Read T R, Cressie N. *Goodness-of-fit statistics for discrete multivariate data*. New York: Springer; 1988.
19. Langeheine R, Pannekoek J, van de Pol F. Bootstrapping goodness-of-fit measures in categorical data analysis, *Sociological Methods and Research*. 1996; 24:492-516.
20. Breathnach C. *Latent class analysis identification of syndromes in Alzheimer's Disease: A Bayesian approach*. Available at http://www.tcd.ie/Statistics/postgraduate/0601.pdf. Accessed Dec. 1, 2008.
21. Lewis-Beck M S, Bryman A, Liao T F. eds. The Sage Encyclopedia of Social Science Research Methods. New York: Sage Publications Inc; 2004.

SUMMARY OF THE INVENTION

In accordance with the invention, a method is implemented on at least one computer, for analyzing the likelihood of biomedical factors contributing to a greater risk of falling in humans, comprising: inputting base data into at the least one computer, the base data including dependent variables representing biomedical factors associated with the humans; and calculating, using the at least one computer, results of a latent class analysis based on the inputted data, using the formula $$f(x_j) = \sum_{k=1}^{K} \eta_k \prod_{i=1}^{1} \pi_{ik}^{x_{ij}} (1 - \pi_{ik})^{(1-x_{ij})},$$

to determine a correlation between the biomedical factors and a probability of falling.

Additional embodiments of the invention include inputting covariate data into the at least one computer corresponding to the number of medications taken by humans, and calculating, using the at least one computer and the results, a changed probability of falling based on the covariate data; inputting covariate data into the at least one computer corresponding to the age of humans, and calculating, using the at least one computer and the results, a changed probability of falling based on the covariate data; inputting covariate data into the at least one computer corresponding to the age of humans and the number of medications taken by humans, and calculating, using the at least one computer and the results, a changed probability of falling based on the covariate data; calculating, using the at least one computer, a posterior probability of an individual belonging to a latent class, using the formula $$h(z_j = k \mid x_j) = \frac{\eta_k \prod_{i=1}^{1} \pi_{ik}^{x_{ij}} (1 - \pi_{ik})^{(1-x_{ij})}}{f(x_j)}.$$

Further in accordance with the invention, biomedical factors are selected from the group consisting of the following: arthritis, high blood pressure, diabetes, foot disorders, Parkinson's Disease, stroke, eye disorder, limb disorder, proprioceptive disorder, cardiovascular disease, musculoskeletal disease, neurological disease, metabolic disease, respiratory disease, diseases and disorders of the nervous system, diseases and disorders of the eye, diseases and disorders of the ear, diseases and disorders of the nose, diseases and disorders of the mouth, diseases and disorders of the throat, diseases and disorders of the respiratory system, diseases and disorders of the circulatory system, diseases and disorders of the digestive system, diseases and disorders of the hepatobiliary system, diseases and disorders of the pancreas, diseases and disorders of the musculoskeletal system, diseases and disorders of the connective tissue, diseases and disorders of the skin, diseases and disorders of the subcutaneous tissue, diseases and disorders of the breast, diseases and disorders of the endocrine system, diseases and disorders of nutrition, diseases and disorders of metabolism, diseases and disorders of the blood, diseases and disorders of blood forming organs, diseases and disorders of the immune system, myeloproliferative diseases and disorders, diseases and disorders of poorly differentiated neoplasms, and significant trauma.

In additional embodiments of the invention, the likelihood of falling is analyzed for an individual human; and graphically displaying, using the at least one computer, probabilities of humans in each latent class being associated with the biomedical factors.

In yet another embodiment of the invention, a method is provided for analyzing the likelihood of biomedical factors contributing to a greater risk of falling in humans, comprising: calculating, based on data including dependent variables representing biomedical factors pertaining to the health of humans, results of a latent class analysis based on the inputted data, using the formula $$f(x_j) = \sum_{k=1}^{K} \eta_k \prod_{i=1}^{1} \pi_{ik}^{x_{ij}} (1 - \pi_{ik})^{(1-x_{ij})},$$

to determine a correlation between the biomedical factors and a probability of falling.

In an alternative embodiment, a computer program product for analyzes the likelihood of biomedical factors contributing to a greater risk of falling in humans, the computer program product comprising instructions which perform the following functions when executed on at least one computer: retrieving data from storage or memory connected to the least one computer, the data including dependent variables representing biomedical factors associated with the humans; and calculating, using the at least one computer, results of a latent class analysis based on the inputted data, using the formula $$f(x_j) = \sum_{k=1}^{K} \eta_k \prod_{i=1}^{1} \pi_{ik}^{x_{ij}} (1 - \pi_{ik})^{(1-x_{ij})},$$

to determine a correlation between the biomedical factors and a probability of falling.

In an embodiment of the invention, xj is the response vector of individual human j taken from a sample of J individuals, xij is the presence or absence of a response $1, \ldots, i/\epsilon$, Πik is the probability of a positive response on variable i for an individual in class z_j=k, $1, \ldots, k$ K $\epsilon$ and ηk are the probability that a randomly chosen individual is in class k, and given the class zj=k and the j individual, independence yields $$f(x_j \mid z_j = k) = \prod_{i=1}^{1} \pi_{ik}^{x_{ij}} (1 - \pi_{ik})^{(1-x_{ij})}.$$

In yet another embodiment of the invention, a computer system analyzes the likelihood of biomedical factors contributing to a greater risk of falling in humans, comprising: at least one computer; storage or memory means connected to the at least one computer for storing base data including dependent variables representing biomedical factors associated with the humans; a processor connected to the computer operative to calculate results of a latent class analysis based on the stored base data, using the formula $$f(x_j) = \sum_{k=1}^{K} \eta_k \prod_{i=1}^{1} \pi_{ik}^{x_{ij}} (1 - \pi_{ik})^{(1-x_{ij})},$$

to determine a correlation between the biomedical factors and a probability of falling; and means for communicating the calculated results, whereby they may be used to further understand, and potentially reduce, incidence of falling.

In an embodiment, the means for communicating includes means for presenting the results on a computer display screen by transforming the results from non-visible digital values stored in the memory of a computer to visible pixels corresponding to human readable characters on the display screen.

In an alternative embodiment of the invention, a method of the invention further includes changing biomedical factors associated with at least one of the humans; performing the step of calculation after the step of changing; determining a change in the likelihood of falling for the at least one human. In various embodiments, the biomedical factors changed includes changing a medication or a dosage of a medication of the at least one human; and the biomedical factors changed includes remediating a disease or disorder of the at least one human.

In another embodiment of the invention, changed data is retrieved changed into the at least one computer, after the step of calculating, the changed data pertaining to biomedical factors associated with at least one of the humans that has changed since the step of calculating; recalculating, using the at least one computer, the step of calculating after the step of retrieving changed data; and calculating, using the at least one computer, a change in the likelihood of falling for the at least one human, between the step of calculating, and the step of recalculating.

In an embodiment thereof, the biomedical factors changed includes a change in a medication or a dosage of a medication relating to the at least one human.

In yet another embodiment of the invention, the storage or memory means further stores changed data pertaining to biomedical factors associated with at least one of the humans that has changed relative to the base data; and wherein the processor connected to the computer is operative to calculate results of the latent class analysis based on the changed data, and to calculate a difference between the results of calculations based on the base data and calculations based on the changed data; and wherein the means for communicating is operative to communicate results pertaining to the calculated difference. In an embodiment, the biomedical factors changed includes a change in a medication or a dosage of a medication relating to the at least one human.

DETAILED DESCRIPTION OF THE INVENTION

All references cited herein are expressly incorporated by reference in their entirety.

Predicting elderly falling can be complex. The present invention increases predictive accuracy, potentially reducing the great economic and human costs associated with falls. The invention further better identifies candidates who have a greater likelihood of falling, so that preventative measures may be taken.

The invention employs latent class analysis (LCA) in a three step modeling approach. First, an optimal number of latent Classes are determined for a set of binary biomedical indicators or variables. Second, two covariates are modeled on the latent classes. Third, the appropriate latent class structure, with the covariates, is modeled on the distal outcome (fall/no fall). The default estimator is maximum likelihood with robust standard errors. The Pearson chi-square, likelihood ratio chi-square, BIC (Bayesian Information Criterion), Lo-Mendell-Rubin Adjusted Likelihood Ratio test and the bootstrap likelihood ratio test are used for model comparisons.

Figure 1:
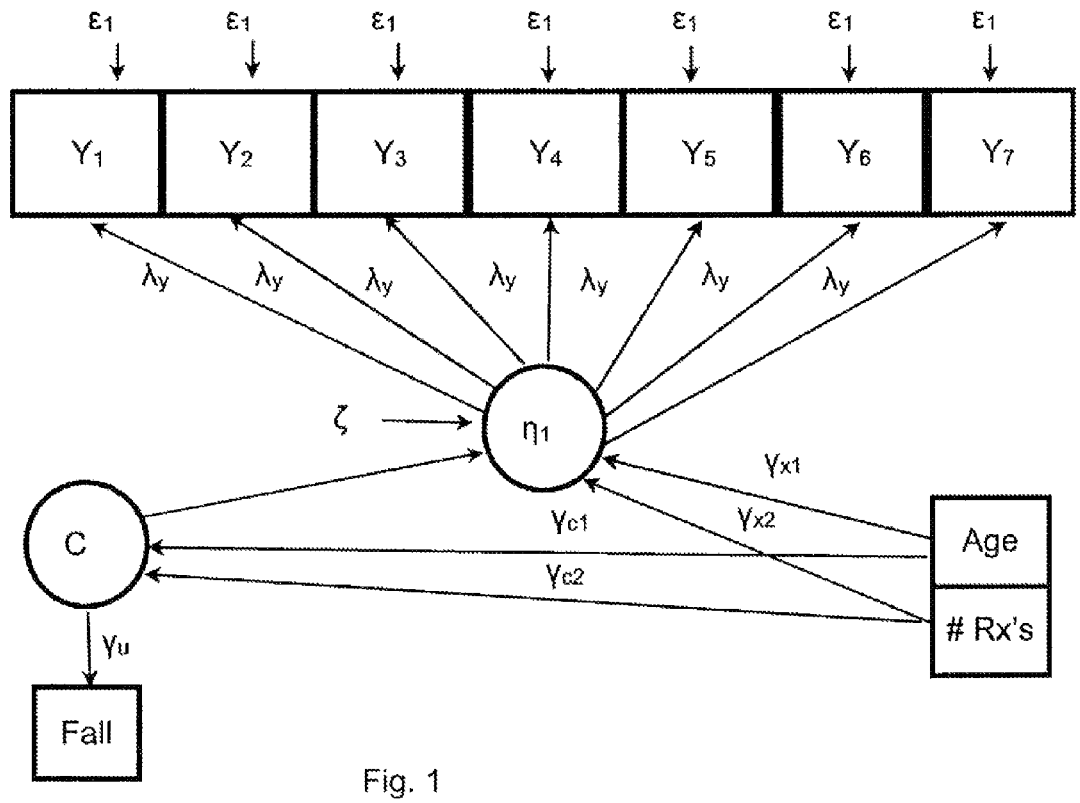
FIG. 1 is a graphical representation of a latent class analysis in accordance with the invention.

In accordance with the invention, a two-class distal outcome, comprising fall and no fall, is determined based upon biomedical and demographic variables. A binary outcome is whether or not a fall occurred. The invention identifies items that indicate classes, estimates class probabilities, relates the class probabilities to covariates, and predicts a distal outcome (fall/no-fall) based on class membership. The process is modeled through the application of a latent class analysis, as shown in FIG. 1, and as described below.

To employ the latent class analysis, latent classes are defined with variables which are independent from each other. The variables are selected based upon the experience of the inventor, and including variables which are believed to contribute to the incidence of a fall. In addition, the presence or absence of one variable is advantageously unrelated to the presence or absence of any other. To carry out the invention, the presence or absence, in a study population, of the following binary biomedical variables may be selected, although it should be understood that additional, fewer, or alternative biomedical factors may be employed within the spirit and scope of the invention: arthritis, high blood pressure, diabetes, foot disorders, Parkinson's Disease, and stroke. Variables which may also or alternatively be relevant include, for example, musculoskeletal disease, neurological disease, metabolic disease, and respiratory disease; although, as a practical matter, the studied subset was defined as described herein, in this embodiment.

More particularly, other biomedical variables which are likely to influence falling, and which are advantageously analyzed in accordance with the invention include: diseases and disorders of the nervous system, diseases and disorders of the eye, diseases and disorders of the ear, diseases and disorders of the nose, diseases and disorders of the mouth, diseases and disorders of the throat, diseases and disorders of the respiratory system, diseases and disorders of the circulatory system, diseases and disorders of the digestive system, diseases and disorders of the hepatobiliary system, diseases and disorders of the pancreas, diseases and disorders of the musculoskeletal system, diseases and disorders of the connective tissue, diseases and disorders of the skin, diseases and disorders of the subcutaneous tissue, diseases and disorders of the breast, diseases and disorders of the endocrine system, diseases and disorders of nutrition, diseases and disorders of metabolism, diseases and disorders of the blood, diseases and disorders of blood forming organs, diseases and disorders of the immune system, myeloproliferative diseases and disorders, diseases and disorders of poorly differentiated neoplasms, and significant trauma.

Binary components are coded as 1 if any and 0 if none, when generating input for the analysis. The model contains the possibility of using continuous variables as predictors (independent variables), dependent variables, and distal outcomes.

Covariates included the age and the number of prescription medications being taken by the study subject, although additional, fewer, or alternative covariates may be selected within the spirit and scope of the invention.

The model for LCA can be described in terms of manifest variables x, and latent categorical variable z [20]. In this case, interest is on manifest variables which consist of a number of binary indicators for each individual, being presence or absence of a particular response [20]. Let xj be the response vector of individual j taken from a sample of J individuals. Then xij is the presence or absence of a response 1, ..., i/ϵ. Let Πik be the probability of a positive response on variable i for a person in class z_j=k 1, ..., k K ϵ and ηk be the probability that a randomly chosen individual is in class k. Given the class zj=k and the j individual, independence yields [20]:

$$f(x_j \mid z_j = k) = \prod_{i=1}^{1} \pi_{ik}^{x_{ij}} (1 - \pi_{ik})^{(1-x_{ij})}.$$

With K classes, the mixture becomes $$f(x_j) = \sum_{k=1}^{K} \eta_k \prod_{i=1}^{1} \pi_{ik}^{x_{ij}} (1 - \pi_{ik})^{(1-x_{ij})}$$

The posterior probability that an individual with response xj belongs to class k is $$h(z_j = k \mid x_j) = \frac{\eta_k \prod_{i=1}^{1} \pi_{ik}^{x_{ij}} (1 - \pi_{ik})^{(1-x_{ij})}}{f(x_j)}.$$

A graphical illustration of a latent class analysis in accordance with the invention is provided in FIG. 1. As should be clear from the preceding, as a practical matter, a computer is used to implement the iterative and computationally intensive steps necessary in order carry out the invention.

Computing System

Figure 4:
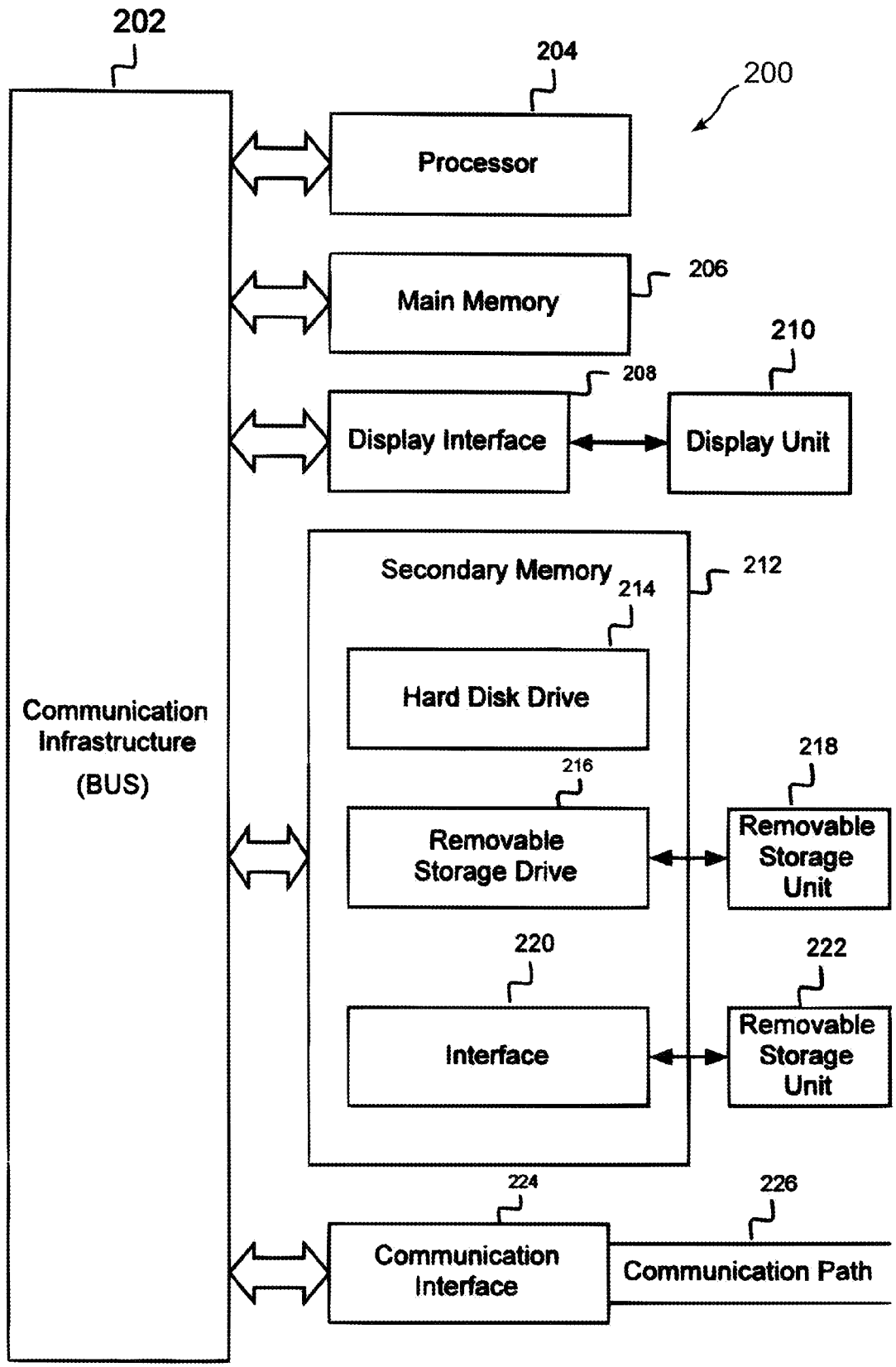
FIG. 4 illustrates a computing system upon which the invention may be implemented.

FIG. 4 is a high level block diagram illustrating a computing system 200 useful for implementing the various embodiments of the present invention.

The computing system 200 is based upon a suitably configured processing system adapted to implement an exemplary embodiment of the present invention. For example, a personal computer, workstation, or the like, may be used. In one embodiment of the present invention, the computing system 200 includes one or more processors, such as processor 204. The processor 204 is connected to a communication infrastructure 202 (e.g., a communications bus, crossover bar, or network). Various software embodiments are described in terms of this exemplary computer system. After reading this description, it becomes apparent to a person of ordinary skill in the relevant art(s) how to implement the invention using other computer systems and/or computer architectures.

The computing system 200 can include a display interface 208 that forwards graphics, text, and other data from the communication infrastructure 202 (or from a frame buffer) for display on the display unit 210. The computing system 400 also includes a main memory 206, preferably random access memory (RAM), and may also include a secondary memory 212 as well as various caches and auxiliary memory as are normally found in computer systems. The secondary memory 212 may include, for example, a hard disk drive 214 and/or a removable storage drive 216, representing a floppy disk drive, a magnetic tape drive, an optical disk drive, and the like. The removable storage drive 216 reads from and/or writes to a removable storage unit 218 in a manner well known to those having ordinary skill in the art.

Removable storage unit 218, represents a floppy disk, a compact disc, magnetic tape, optical disk, etc. which is read by and written to by removable storage drive 216. As are appreciated, the removable storage unit 218 includes a computer readable medium having stored therein computer software and/or data. The computer readable medium may include non-volatile memory, such as ROM, Flash memory, Disk drive memory, CD-ROM, and other permanent storage. Additionally, a computer medium may include, for example, volatile storage such as RAM, buffers, cache memory, and network circuits. Furthermore, the computer readable medium may comprise computer readable information in a transitory state medium such as a network link and/or a network interface, including a wired network or a wireless network that allow a computer to read such computer-readable information.

In alternative embodiments, the secondary memory 212 may include other similar means for allowing computer programs or other instructions to be loaded into the computing system 200. Such means may include, for example, a removable storage unit 222 and an interface 220. Examples of such may include a program cartridge and cartridge interface (such as that found in video game devices), a removable memory chip (such as an EPROM, or PROM) and associated socket, and other removable storage units 222 and interfaces 220 which allow software and data to be transferred from the removable storage unit 222 to the computing system 200.

The computing system 200, in this example, includes a communications interface 224 that acts as an input and output and allows software and data to be transferred between the computing system 200 and external devices or access points via a communications path 226. Examples of communications interface 224 may include a modem, a network interface (such as an Ethernet card), a communications port, a PCM-CIA slot and card, etc. Software and data transferred via communications interface 224 are in the form of signals which may be, for example, electronic, electromagnetic, optical, or other signals capable of being received by communications interface 224. The signals are provided to communications interface 224 via a communications path (i.e., channel) 226. The channel 226 carries signals and may be implemented using wire or cable, fiber optics, a phone line, a cellular phone link, an RF link, and/or other communications channels.

In this document, the terms "computer program medium," "computer usable medium," "computer readable medium", "computer readable storage product", and "computer program storage product" are used to generally refer to media such as main memory 206 and secondary memory 212, removable storage drive 216, and a hard disk installed in hard disk drive 214. The computer program products are means for providing software to the computer system. The computer readable medium allows the computer system to read data, instructions, messages or message packets, and other computer readable information from the computer readable medium.

Computer programs (also called computer control logic) are stored in main memory 406 and/or secondary memory 212. Computer programs may also be received via communications interface 224. Such computer programs, when executed, enable the computer system to perform the features of the various embodiments of the present invention as discussed herein. In particular, the computer programs, when executed, enable the processor 204 to perform the features of the computer system.

Example

A data set consisting of 3,293 elderly patients is analyzed. Seventy-four percent of the subjects had not fallen while 26 percent had fallen in the last 30 days. Descriptive statistics for the data set are as follows:

TABLE 1

Descriptive Statistics

|  |  | No Fall | Fall |
|---|---|---|---|
| Age | Mean ± SD | 77.47 ± 6.91 | 77.98 ± 7.41 |
| Medications | Mean ± SD | 2.30 ± 5.57 | 5.10 ± 10.10 |
| Gender | Male | 27% | 22% |
|  | Female | 73% | 78% |
| Arthritis | Percent | 69.87 | 30.13 |
| HBP | Percent | 71.58 | 28.42 |
| Diabetes | Percent | 66.14 | 33.86 |
| Heart Disease | Percent | 66.71 | 33.29 |
| Foot Disorder | Percent | 65.27 | 34.73 |
| Parkinsons Disease | Percent | 58.67 | 41.33 |
| Stroke | Percent | 62.16 | 37.84 |

Falling is defined as "an event which results in the person coming to rest inadvertently on the ground or other lower level, and other than as a consequence of sustaining a violent blow."

With reference to Table 2, below, an initial review of the model fit indices, with no covariates, indicated a five-class solution to be advantageous. More particularly, the posterior probability of membership in latent class t, given response vector y for subject s equals a ratio in which the numerator is the product of the latent class proportion times the probability of response vector ys assuming membership in latent class t; and the denominator is the unconditional probability for response vector y. Computationally, Bayes' theorem is applied for each latent class and then all cases with a given response vector are classified into the latent class for which the posterior probability is highest. The probabilities are a function of the model's parameters (estimated conditional response probabilities and estimated prevalence of each latent class). Each case is assigned to the latent class for which it has the highest a posteriori (Bayesian) probability of membership. Alternatively, the same methods can assign each case a probability of membership in each latent class.

Advantageously, the members of each class are distinguished from the members of the remaining classes, ideally to the largest extent possible. An optimal number of classes is selected which best represents distinct and useful groupings of individuals. This may be observed, for example, in Table 4, where a relatively high percentage of individuals fit each respective class. The preponderance of specific biomedical factors in each class may then be used to identify individuals who are at risk of falling, whereupon steps may be taken to reduce the likelihood of falling on a patient by patient basis, or for any person who might otherwise currently or potentially share the biomedical factors of the class. It was determined, for these biomedical factors, that a five-class solution provided a lower BIC (lower is better), much smaller chi-square values, and as indicated by the bootstrap procedures (LMR and BLRT) the five-class solution had advantageous non-significant p-values.

Figure 3:
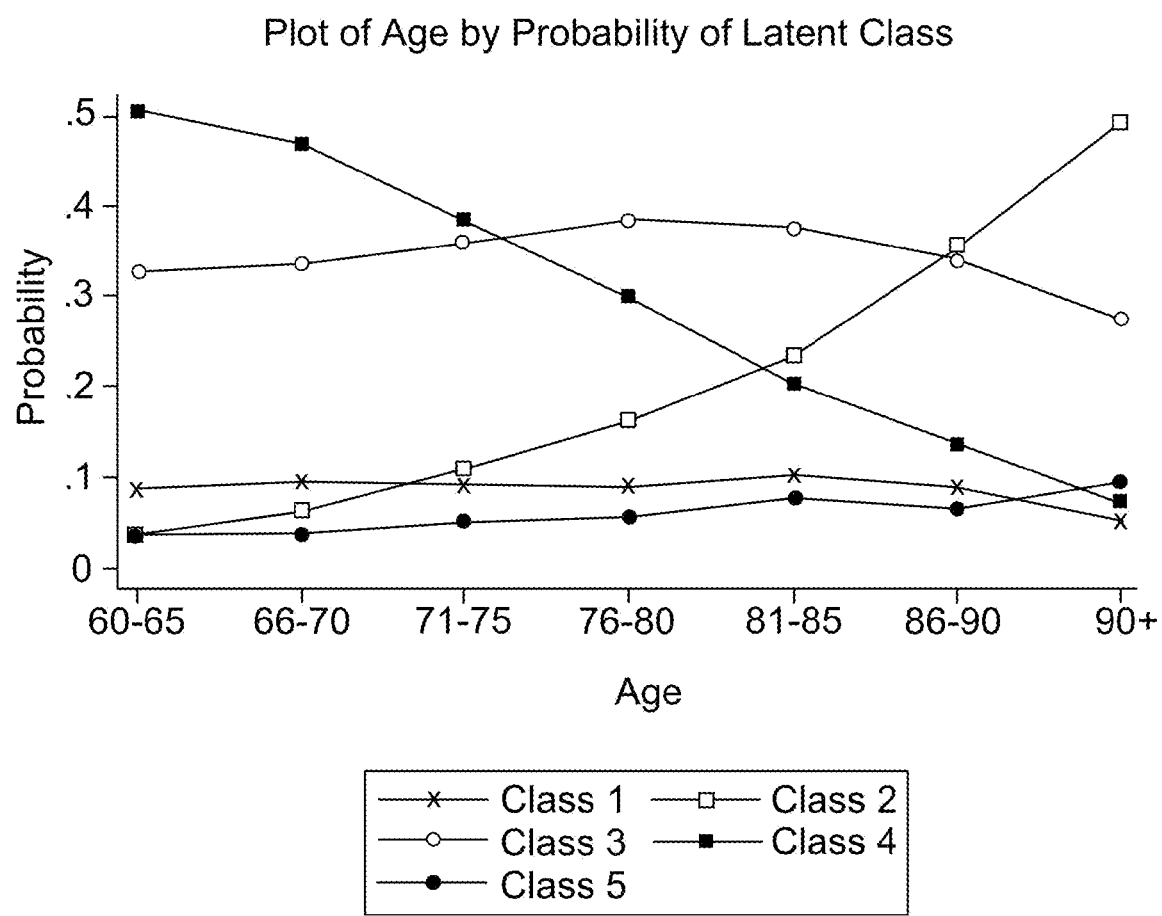
FIG. 3 is a plot of age by probability of latent class.

Next, the five-class solution was modeled with the covariates of age and number of prescription medications, on the distal outcome—fall or no fall. Specifically, age and the number of medications were analyzed for each class using multinomial logistic regression, to determine an effect of the covariate on the class. With reference to FIG. 3, age was shown to be non-significant but was left in the model because age has been shown to significantly influence the probability of falling [10]. The number of prescription medications demonstrated a significant impact on falling. More particularly, the more prescription drugs an elderly person takes, the greater the probability that they will fall. Table 2 provides a comparison of fit indices for two-class, three-class, four-class, five-class, and six class solutions, as well as five class with covariates and distal outcome.

TABLE 2

Basic Latent Class Structure

|  | Two Class | Three Class | Four Class | Five Class | Six Class | 5 Class w/ Covariates & Distal Outcome |
|---|---|---|---|---|---|---|
| Pearson $X^2$ | 346 | 253 | 206 | 165 | 84 | 518 |
| LR $X^2$ | 346 | 204 | 153 | 109 | 84 | 411 |
| $X^2$ df | 112 | 104 | 96 | 88 | 80 | 215 |
| Loglikelihood | −10,591 | −10,520 | −10,494 | −10,472 | −10,460 | −12,222 |
| Number of Parameters | 15 | 23 | 31 | 39 | 47 | 52 |
| BIC | 21,303 | 21,226 | 21,240 | 21,261 | 21,301 | 24,866 |
| LMR (p value) | 0.000 | 0.000 | 0.000 | 0.355 | 0.491 | 0.400 |
| BLRT (p value) | 0.000 | 0.000 | 0.000 | 0.359 | 0.495 | 0.410 |
| Entropy | 0.545 | 0.591 | 0.633 | 0.604 | 0.585 | 0.558 |

The five class structures, with covariates, may be interpreted, with reference to the following tables, as follows:

TABLE 3

Final Class Counts and Proportions Based on Posterior Probabilities

|  | Count | Proportion (%) |
|---|---|---|
| 1 | 312 | 9 |
| 2 | 580 | 18 |
| 3 | 1190 | 36 |
| 4 | 1016 | 31 |
| 5 | 195 | 6 |
| Total | 3293 | 100 |

TABLE 4

Most Likely Latent Class Membership

| | Class 1 (%) | Class 2 (%) | Class 3 (%) | Class 4 (%) | Class 5 (%) |
|---|---|---|---|---|---|
| 1 | 72 | 7 | 0 | 19 | 1 |
| 2 | 5 | 60 | 11 | 19 | 5 |
| 3 | 0 | 11 | 75 | 10 | 5 |
| 4 | 7 | 11 | 9 | 70 | 3 |
| 5 | 4 | 8 | 11 | 16 | 61 |

TABLE 5

Odds Ratios*

| Class | Odds | Lower 95% | Upper 95% | P Value |
|---|---|---|---|---|
| 1.00 | 3.32 | 2.49 | 4.15 | 0.00 |
| 2.00 | 2.63 | 2.03 | 3.40 | 0.00 |
| 4.00 | 1.63 | 1.32 | 2.03 | 0.00 |
| 5.00 | 39.32 | 21.64 | 71.45 | 0.00 |
| Age | 1.00 | 0.98 | 1.01 | 0.69 |
| Number of Medications | 1.01 | 1.00 | 1.09 | 0.00 |

*Base or comparison group is class three or the "healthy" group

Figure 2:
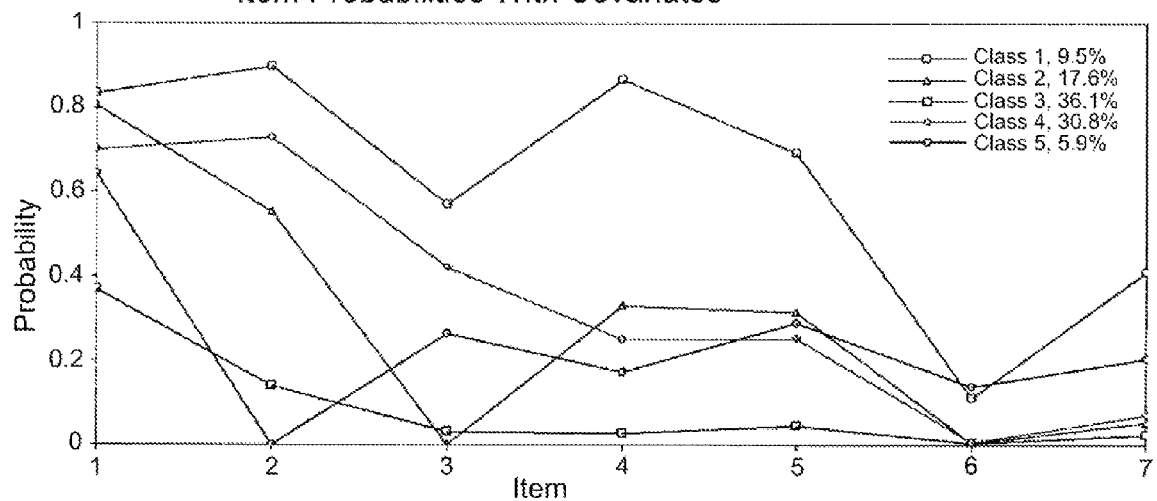
FIG. 2 is a graphical representation of an item probability graph, generated in accordance with the invention, of data from the Example detailed herein.

Class one is most likely to be affected by all medical conditions except for Parkinson's Disease (FIG. 2). For convenience, this is defined as the poorest-health group. Nine percent of the sample is classified into latent class one (Table 3). The predictive probability for latent class one is 72% (Table 4). The misclassified elderly generally were placed into class two or class four. The odds ratio indicate that a person in class one is three times more likely to fall than a person in class three—the healthy group (Table 5).

Class two is primarily affected by arthritis and to a lesser extent high blood pressure (FIG. 1). For convenience, this is defined as the arthritis group. Eighteen percent of the sample was placed into latent class two (Table 3). Of all the latent classes, class two possessed the poorest predictive validity (60%—Table 4). Misclassified elderly were placed into either class three (healthy group) or four (high blood pressure group). The odds ratio indicate that a person in class two is about 2.5 times more likely to fall than a person in class three—the healthy group (Table 5).

Class three is generally unaffected by all medical markers (FIG. 2). For convenience, this is defined as the healthy group. The majority of elderly (31%—Table 3) in our sample were classified into latent class three. Of all groups, class three possessed the best predictive validity (75%—Table 4). Misclassified elderly were placed into either class two or four. We used this as our comparison group for the calculation of odds ratios for falling.

Class four is primarily affected by high blood pressure (HBP), but also arthritis and diabetes (FIG. 2). For convenience, this is defined as the HBP group. Thirty-one percent of this sample fell into latent class four (Table 3). Class four possessed adequate predictive validity (70%—Table 4). Misclassified elderly were placed into either class two (arthritis) or three (healthy group). The odds ratio indicate that a person in class four is approximately 1.5 times more likely to fall than a person in class three—the healthy group (Table 5).

Class five is primarily affected by Parkinson's Disease. For convenience, this is defined as the Parkinson's group. Six percent of the sample fell into latent class five (Table 3). Class five possessed average predictive validity (61%—Table 4). The relatively poor classification rate is probably due to the small number of elderly who possessed Parkinson's Disease. Misclassified elderly were placed into either class four (HBP) or three (healthy group). The odds ratio indicates that a person in class five is 39 times more likely to fall than a person in class three—the healthy group (Table 5). This strongly indicates that a person with Parkinson's Disease is very likely to fall.

The invention thus demonstrates that a latent class analysis can be applied to biomedical factors associated with falling, in order to better understand the likelihood of falling based upon the presence of those biomedical factors in individuals or a population. More particularly, the invention demonstrates the utility of LCA in the measurement of falling among community-dwelling elderly. LCA is used in accordance with the invention to identify subgroups based upon parameters of a postulated statistical model. The subgroups form the categories of a categorical latent variable. The use of LCA in accordance with the invention further greatly improves adjustment for a misclassified confounding variable. The five-class solution is found to be statistically sound and provides a relatively straightforward interpretable number of classes. The interpretation of a LCA relies on both the statistical indices and the practical interpretation of the classes. In accordance with the invention, the statistical indices strongly point towards a five factor model. The positive predictive values for both models (with and without a distal outcome) were acceptable. Furthermore, the invention enables a definition of each latent class, which provides researchers and practitioners practical implications of the analysis.

The invention successfully predicts group membership for class three 75 percent of the time. The majority of elderly who should have been placed into class three were identified as persons in class four—high blood pressure group. A review of FIG. 2 demonstrates that the probability of item endorsement for class three and four generally parallels each other. The primary difference between the groups is the likelihood that an elderly patient possess a specific medical condition. Elderly community dwellers in class four possess a greater probability of having each medical condition than elderly in class three. Given that elderly in class four possess greater odds of falling, this would make rational sense.

It is noted that categorization of persons into class two and five was less definitive than the other classes. Class two is the arthritis group and class five is the Parkinson's Disease group. The majority of misclassified elderly for the class two and five were placed into class four (19% and 16% respectively). This misclassification may be to the fact that all three groups, classes two, four and five, possess high probabilities of having arthritis.

Examining the odds ratios indicates that class two and four possess similar odds of falling, but class five has much greater odds. Class five's greater likelihood of falling is primarily due to Parkinson's Disease. Therefore, it is probable given additional biomedical conditions, these three classes may better differentiate.

Class one possessed an above average classification rate of 72 percent (Table 4). A review of the item probability graph in FIG. 2 shows that the elderly in class one possess the greatest likelihood of possessing all medical conditions except for Parkinson's Disease. Furthermore, elderly in class one had the second highest probability of falling. Similar to all other classes, misclassified elderly were placed into class four (19%). This pattern of misclassification appears to suggest that because many of the elderly possess the medical conditions, adding additional items or covariates may be advantageous.

In a health care setting, the invention may be advantageously employed to follow a risk-factor modification strategy which allows health care professionals to calculate individual risk profiles. Risk profiles provide the documentation necessary to connect the relationship between individual risk factors (biomedical, pharmacological, or demographic) and fall prevention strategies. The invention provides health care professionals with at least the following two measures:

The absolute probability of falling based on all analyzed biomedical, pharmacological, and demographic factors. For example, Patient A may have an 80% risk of falling based on age, diabetes and use of Medication J with Dosage I.

The relative probability for each risk factor is based on each risk factor's contribution to the absolute probability of falling. For example, Patient A may have an 80% risk of falling based on (a) age which contributes 10% to the absolute risk of falling, (b) diabetes which contributes 20% to the absolute risk of falling, (c) the use of Medication J which contributes 30% to the absolute risk of falling, and (d) Dosage I which also contributes 30% to the absolute risk of falling.

A fall risk modification strategy would review and adjust the appropriate risk factor using the methodology of the invention as described herein. In the example above, the physician could substitute a new medication or change the dosage, to reduce both the absolute and relative probability of falling. Individual risk profiles would be continually monitored and updated thereby continuing the fall risk-factor modification strategy, and reducing the risk of falling for the individual. An analysis in accordance with the invention may advantageously be carried out in an iterative process, as factors associated with patients are changed, and additional statistical information is obtained. For example, a medication, or a dosage, may be changed based upon results of an analysis in accordance with the invention, or based upon an hypothesis, and a further or initial analysis in accordance with the invention performed. If there is an initial, or base set of data, results of an analysis of this data may be compared with results of data based on the changed parameters. The difference between results of the base data and the changed data may be studied and used to reduce a likelihood of falling for individual patients, or for a population of patients.

The invention provides an effective method for finding relevant subgroups with a heterogenous at-risk population for falling, as well as a valuable tool to model medical data. It is noted that the data in the example provided was not gathered with an analysis in accordance with the invention in mind. However, while the five-class solution described above is demonstrated to be a sound model, providing good predictive validity for elderly falling, a study designed a priori may enable improved predictions. Moreover, it should be understood that data for other biomedical factors, for example eye, limb, or proprioceptive disease or disorder, may be used in accordance with the invention with potentially advantageous results.

It will be appreciated by persons skilled in the art that the present invention is not limited to what has been particularly shown and described herein above. A variety of modifications and variations are possible in light of the above teachings without departing from the scope and spirit of the invention.

What is claimed is:

1. A method, implemented on at least one computer, for analyzing a likelihood of biomedical factors contributing to a greater risk of falling in humans, comprising:
   inputting base data into the at least one computer, the base data including dependent variables representing biomedical factors associated with the humans; and
   calculating, using the at least one computer, results of a latent class analysis based on the inputted base data, using the formula $$f(x_j) = \sum_{k=1}^{K} \eta_k \prod_{i=1}^{1} \pi_{ik}^{x_{ij}} (1 - \pi_{ik})^{(1-x_{ij})},$$

to determine a correlation between the biomedical factors and a probability of falling,
   where $x_j$ is the response vector of an individual j taken from a sample of J individuals, $x_{ij}$ is the presence or absence of a response on variable i for an individual j in class k, $\Pi_{ik}$ is the probability of a positive response on variable i for an individual in class k and $\eta_k$ is the probability that a randomly chosen individual is in class k, and K is the number of classes.

2. The method of claim 1, further comprising:
   inputting covariate data into the at least one computer corresponding to a number of medications taken by humans;
   calculating, using the at least one computer and said results, a changed probability of falling based on the covariate data.

3. The method of claim 1, further comprising:
   inputting covariate data into the at least one computer corresponding to an age of humans;
   calculating, using the at least one computer and said results, a changed probability of falling based on the covariate data.

4. The method of claim 1, further comprising:
   inputting covariate data into the at least one computer corresponding to an age of humans and a number of medications taken by humans;
   calculating, using the at least one computer and said results, a changed probability of falling based on the covariate data.

5. The method of claim 1, further comprising:
   calculating, using the at least one computer, a posterior probability of an individual belonging to a latent class, using the formula $$h(z_j = k \mid x_j) = \frac{\eta_k \prod_{i=1}^{1} \pi_{ik}^{x_{ij}} (1 - \pi_{ik})^{(1-x_{ij})}}{f(x_j)}.$$

where $z_j$ is the class of an individual j.

6. The method of claim 1, wherein said biomedical factors are selected from the group consisting of the following: arthritis, high blood pressure, diabetes, foot disorders, Parkinson's Disease, stroke, eye disorder, limb disorder, proprioceptive disorder, cardiovascular disease, musculoskeletal disease, neurological disease, metabolic disease, respiratory disease, diseases and disorders of the nervous system, diseases and disorders of the eye, diseases and disorders of the ear, diseases and disorders of the nose, diseases and disorders of the mouth, diseases and disorders of the throat, diseases and disorders of the respiratory system, diseases and disorders of the circulatory system, diseases and disorders of the digestive system, diseases and disorders of the hepatobiliary system, diseases and disorders of the pancreas, diseases and disorders of the musculoskeletal system, diseases and disorders of the connective tissue, diseases and disorders of the skin, diseases and disorders of the subcutaneous tissue, diseases and disorders of the breast, diseases and disorders of the endocrine system, diseases and disorders of nutrition, diseases and disorders of metabolism, diseases and disorders of the blood, diseases and disorders of blood forming organs, diseases and disorders of the immune system, myeloproliferative diseases and disorders, diseases and disorders of poorly differentiated neoplasms, and significant trauma.

7. The method of claim 1, wherein a likelihood of falling is analyzed for an individual human.

8. The method of claim 1, further comprising:
graphically displaying, using the at least one computer, probabilities of humans in each latent class being associated with the biomedical factors.

9. The method of claim 1, where xj is the response vector of individual human j taken from a sample of J individuals, xij is the presence or absence of a response 1, ..., i/ϵ, Πik is the probability of a positive response on variable i for an individual in class z_j=k, 1, ..., k K ϵ and ηk are the probability that a randomly chosen individual is in class k, and given the class zj=k and the j individual, independence yields $$f(x_j \mid z_j = k) = \prod_{i=1}^{1} \pi_{ik}^{x_{ij}} (1 - \pi_{ik})^{(1-x_{ij})}.$$

where z_j=$z_j$.

10. The method of claim 1, further including:
inputting changed data into the at least one computer, the changed data pertaining to biomedical factors associated with at least one of the humans that has changed relative to the base data;
performing said step of calculation after said step of inputting changed data;
determining a change in a likelihood of falling for the at least one human based upon a difference between said base data and said changed data.

11. The method of claim 10, wherein said biomedical factors changed include changing a medication or a dosage of a medication of the at least one human.

12. The method of claim 10, wherein said biomedical factors changed include remediating a disease or disorder of the at least one human.

13. A computer program product comprising a non-transitory computer readable storage medium for analyzing a likelihood of biomedical factors contributing to a greater risk of falling in humans, the computer program product comprising instructions which perform the following functions when executed on at least one computer:
retrieving data from non-transitory storage or memory connected to the least one computer, the data including dependent variables representing biomedical factors associated with the humans; and
calculating, using the at least one computer, results of a latent class analysis based on the inputted data, using the formula $$f(x_j) = \sum_{k=1}^{K} \eta_k \prod_{i=1}^{1} \pi_{ik}^{x_{ij}} (1 - \pi_{ik})^{(1-x_{ij})},$$

to determine a correlation between the biomedical factors and a probability of falling, where $x_j$ is the response vector of an individual j taken from a sample of J individuals, $x_{ij}$ is the presence or absence of a response on variable i for an individual j in class k, $\Pi_{ik}$ is the probability of a positive response on variable i for an individual in class k and $\eta_k$ is the probability that a randomly chosen individual is in class k, and K is the number of classes.

14. The product of claim 13, further including:
retrieving changed data into the at least one computer, after said step of calculating, said changed data pertaining to biomedical factors associated with at least one of the humans that has changed since said step of calculating;
recalculating, using the at least one computer, said step of calculating after said step of retrieving changed data; and
calculating, using the at least one computer, a change in a likelihood of falling for the at least one human, between said step of calculating, and said step of recalculating.

15. The product of claim 14, wherein said biomedical factors changed include a change in a medication or a dosage of a medication relating to the at least one human.

16. A computer system for analyzing a likelihood of biomedical factors contributing to a greater risk of falling in humans, comprising:
at least one computer;
storage or memory means connected to said at least one computer for storing base data including dependent variables representing biomedical factors associated with the humans;
a processor connected to said computer operative to calculate results of a latent class analysis based on the stored base data, using the formula $$f(x_j) = \sum_{k=1}^{K} \eta_k \prod_{i=1}^{1} \pi_{ik}^{x_{ij}} (1 - \pi_{ik})^{(1-x_{ij})},$$

to determine a correlation between the biomedical factors and a probability of falling; and
means for communicating said calculated results, whereby they may be used to further understand, and potentially reduce, incidence of falling,
where $x_j$ is the response vector of an individual j taken from a sample of J individuals, $x_{ij}$ is the presence or absence of a response on variable i for an individual j in class k, $\Pi_{ik}$ is the probability of a positive response on variable i for an individual in class k and $\eta_k$ is the probability that a randomly chosen individual is in class k, and K is the number of classes.

17. The computer system of claim 16, wherein said means for communicating includes means for presenting said results on a computer display screen by transforming said results from non-visible digital values stored in the memory of a computer to visible pixels corresponding to human readable characters on the display screen.

18. The system of claim 16, wherein said storage or memory means further stores changed data pertaining to biomedical factors associated with at least one of the humans that has changed relative to said base data; and
wherein said processor connected to said computer is operative to calculate results of said latent class analysis based on the changed data, and to calculate a difference between said results of calculations based on said base data and calculations based on said changed data; and wherein said means for communicating is operative to communicate results pertaining to said calculated difference.

19. A method for predicting a likelihood of falling in humans, comprising:
using at least one computer executing software stored on non-transitory media, the software configured for:
receiving base data including an optimal number of latent classes for a set of independent binary biomedical indicators associated with falling in humans;
calculating a posterior probability of membership in latent class t, given a response vector y for subject s equals a ratio in which the numerator is the product of a latent class proportion times a probability of response vector ys assuming membership in latent class t; and the denominator is an unconditional probability for response vector y;
receiving data pertaining to one or more covariates; and
calculating, using multinomial logistic regression, an effect of the one or more covariates on at least one latent class.

20. The method of claim 19, wherein the one or more covariates is selected from the group consisting of age and a number of medications.

* * * * *